United States Patent
McLaughlin et al.

(10) Patent No.: US 11,191,927 B2
(45) Date of Patent: Dec. 7, 2021

(54) DILATOR WITH ENGAGEMENT REGION

(71) Applicant: BOSTON SCIENTIFIC SCIMED, INC., Maple Grove, MN (US)

(72) Inventors: Cathal Joseph McLaughlin, Letterkenny (IE); James M. Anderson, Corcoran, MN (US); Roger W. McGowan, Ostego, MN (US); Gregory Dyer, New Brighton, MN (US); Erik Joseph Haun, Maple Grove, MN (US); Shawn M. Wignall, Maple Plain, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 410 days.

(21) Appl. No.: 16/050,295

(22) Filed: Jul. 31, 2018

(65) Prior Publication Data
US 2019/0030294 A1  Jan. 31, 2019

Related U.S. Application Data

(60) Provisional application No. 62/539,140, filed on Jul. 31, 2017.

(51) Int. Cl.
*A61M 5/178* (2006.01)
*A61M 25/06* (2006.01)
(Continued)

(52) U.S. Cl.
CPC ..... *A61M 25/0662* (2013.01); *A61B 17/3439* (2013.01); *A61M 29/00* (2013.01);
(Continued)

(58) Field of Classification Search
CPC ...... A61B 17/3439; A61M 2025/0006; A61M 2025/0024; A61M 2025/0687;
(Continued)

(56) References Cited

U.S. PATENT DOCUMENTS

| 5,117,839 A | 6/1992 | Dance |
| 5,234,437 A | 8/1993 | Sepetka |

(Continued)

FOREIGN PATENT DOCUMENTS

| EP | 2777542 A2 | 9/2014 |
| EP | 2777545 A2 | 9/2014 |

(Continued)

OTHER PUBLICATIONS

International Search Report & Written Opinion dated Jun. 15, 2018 for International Application No. PCT/US2018/021978.
(Continued)

*Primary Examiner* — Rebecca E Eisenberg
(74) *Attorney, Agent, or Firm* — Seager, Tufte & Wickhem, LLP

(57) ABSTRACT

An example dilator is disclosed. The example dilator includes a hub and an elongate shaft having a distal end region, a proximal end region and a cross-sectional profile. Additionally, the proximal end region of the elongate shaft is coupled to the hub and the elongate shaft is configured to extend through at least a portion of a lumen of an expandable introducer sheath. Additionally, the cross-sectional profile of the elongate shaft includes at least one engagement portion and at least a portion of the expandable introducer sheath extends into the at least one engagement portion of the dilator.

19 Claims, 10 Drawing Sheets

(51) Int. Cl.
*A61B 17/34* (2006.01)
*A61M 29/00* (2006.01)
*A61M 25/00* (2006.01)

(52) U.S. Cl.
CPC ..... *A61M 25/0043* (2013.01); *A61M 25/0097* (2013.01); *A61M 2025/0006* (2013.01); *A61M 2025/0024* (2013.01); *A61M 2025/0687* (2013.01)

(58) Field of Classification Search
CPC .......... A61M 25/0043; A61M 25/0097; A61M 25/0662; A61M 29/00
See application file for complete search history.

(56) References Cited

U.S. PATENT DOCUMENTS

| | | | |
|---|---|---|---|
| 5,250,071 A | 10/1993 | Palermo | |
| 5,282,478 A | 2/1994 | Fleischhaker, Jr. et al. | |
| 5,304,195 A | 4/1994 | Twyford, Jr. et al. | |
| 5,312,415 A | 5/1994 | Palermo | |
| 5,546,958 A | 8/1996 | Thorud et al. | |
| RE37,117 E | 3/2001 | Palermo | |
| 6,277,125 B1 | 8/2001 | Barry et al. | |
| 6,491,646 B1 | 12/2002 | Blackledge | |
| 6,589,262 B1 | 7/2003 | Honebrink et al. | |
| 7,044,134 B2 | 5/2006 | Khairkhahan et al. | |
| 7,708,755 B2 | 5/2010 | Davis et al. | |
| 7,815,661 B2 | 10/2010 | Mirizzi et al. | |
| 7,896,899 B2 | 3/2011 | Patterson et al. | |
| 8,142,456 B2 | 3/2012 | Rosqueta | |
| 8,236,042 B2 | 8/2012 | Berez et al. | |
| 8,333,786 B2 | 12/2012 | Mirizzi et al. | |
| 8,333,796 B2 | 12/2012 | Tompkins et al. | |
| 8,641,777 B2 | 2/2014 | Strauss et al. | |
| 8,696,701 B2 | 4/2014 | Becking et al. | |
| 8,747,597 B2 | 6/2014 | Rosqueta et al. | |
| 8,795,313 B2 | 8/2014 | Liang et al. | |
| 8,801,746 B1 | 8/2014 | Kreidler et al. | |
| 8,911,487 B2 | 12/2014 | Bennett et al. | |
| 9,017,350 B2 | 4/2015 | Karabey et al. | |
| 9,017,361 B2 | 4/2015 | Karabey et al. | |
| 9,060,773 B2 | 6/2015 | Nguyen et al. | |
| 9,119,948 B2 | 9/2015 | Lee et al. | |
| 9,186,151 B2 | 11/2015 | Tompkins et al. | |
| 9,198,670 B2 | 12/2015 | Hewitt et al. | |
| 9,301,827 B2 | 4/2016 | Strauss et al. | |
| 9,307,999 B2 | 4/2016 | Li et al. | |
| 9,468,442 B2 | 10/2016 | Huynh et al. | |
| 9,498,226 B2 | 11/2016 | Cage et al. | |
| 9,549,740 B2 | 1/2017 | Rees | |
| 9,554,805 B2 | 1/2017 | Tompkins et al. | |
| 2004/0039332 A1 | 2/2004 | Kantor | |
| 2006/0036281 A1 | 2/2006 | Patterson et al. | |
| 2006/0212055 A1 | 9/2006 | Karabey et al. | |
| 2006/0229669 A1 | 10/2006 | Mirizzi et al. | |
| 2006/0282159 A1 | 12/2006 | Taheri | |
| 2007/0135826 A1 | 6/2007 | Zaver et al. | |
| 2007/0208323 A1* | 9/2007 | Gregorich ............. A61M 25/10 604/523 |
| 2007/0270903 A1 | 11/2007 | Davis et al. | |
| 2007/0282373 A1 | 12/2007 | Ashby et al. | |
| 2007/0293928 A1 | 12/2007 | Tomlin | |
| 2008/0109059 A1 | 5/2008 | Gordon et al. | |
| 2008/0119891 A1 | 5/2008 | Miles et al. | |
| 2008/0300616 A1 | 12/2008 | Que et al. | |
| 2009/0043331 A1 | 2/2009 | Buiser et al. | |
| 2009/0062838 A1 | 3/2009 | Brumleve et al. | |
| 2009/0062845 A1 | 3/2009 | Tekulve | |
| 2009/0088771 A1 | 4/2009 | Nimgaard | |
| 2009/0163934 A1 | 6/2009 | Raschdorf, Jr. et al. | |
| 2009/0177261 A1 | 7/2009 | Teoh et al. | |
| 2009/0270978 A1 | 10/2009 | Virkler et al. | |
| 2009/0287291 A1 | 11/2009 | Becking et al. | |
| 2009/0287294 A1 | 11/2009 | Rosqueta et al. | |
| 2010/0106178 A1 | 4/2010 | Obermiller et al. | |
| 2010/0121350 A1 | 5/2010 | Mirigian | |
| 2010/0174269 A1 | 7/2010 | Tompkins et al. | |
| 2011/0166588 A1 | 7/2011 | Connor et al. | |
| 2011/0184454 A1 | 7/2011 | Barry et al. | |
| 2011/0202085 A1 | 8/2011 | Loganathan et al. | |
| 2011/0238147 A1 | 9/2011 | Bennett et al. | |
| 2011/0265943 A1 | 11/2011 | Rosqueta et al. | |
| 2011/0319926 A1 | 12/2011 | Becking et al. | |
| 2012/0046687 A1 | 2/2012 | Trommeter et al. | |
| 2012/0197299 A1 | 8/2012 | Fabian, Jr. | |
| 2012/0203322 A1 | 8/2012 | Eells | |
| 2012/0283812 A1 | 11/2012 | Lagodzki | |
| 2012/0316598 A1 | 12/2012 | Becking et al. | |
| 2012/0330341 A1 | 12/2012 | Becking et al. | |
| 2012/0330347 A1 | 12/2012 | Becking et al. | |
| 2012/0330348 A1 | 12/2012 | Strauss et al. | |
| 2013/0066360 A1 | 3/2013 | Becking et al. | |
| 2013/0072961 A1 | 3/2013 | Cage et al. | |
| 2013/0085520 A1 | 4/2013 | Liang et al. | |
| 2013/0085522 A1 | 4/2013 | Becking et al. | |
| 2013/0152941 A1 | 6/2013 | Nguyen et al. | |
| 2013/0253572 A1 | 9/2013 | Molaei et al. | |
| 2013/0261730 A1 | 10/2013 | Bose et al. | |
| 2013/0296917 A1 | 11/2013 | Rees | |
| 2013/0331882 A1 | 12/2013 | Tompkins et al. | |
| 2014/0058434 A1 | 2/2014 | Jones et al. | |
| 2014/0058435 A1 | 2/2014 | Jones et al. | |
| 2014/0128907 A1 | 5/2014 | Hui et al. | |
| 2014/0135810 A1 | 5/2014 | Divino et al. | |
| 2014/0135811 A1 | 5/2014 | Divino et al. | |
| 2014/0135812 A1 | 5/2014 | Divino et al. | |
| 2014/0148843 A1 | 5/2014 | Strauss et al. | |
| 2014/0172001 A1 | 6/2014 | Becking et al. | |
| 2014/0236127 A1 | 8/2014 | Lee et al. | |
| 2014/0358175 A1 | 12/2014 | Tompkins et al. | |
| 2015/0005807 A1 | 1/2015 | Lagodzki et al. | |
| 2015/0073524 A1 | 3/2015 | Bennett et al. | |
| 2015/0112378 A1 | 4/2015 | Torp | |
| 2015/0157332 A1 | 6/2015 | Obermiller et al. | |
| 2015/0196304 A1 | 7/2015 | Rabkin et al. | |
| 2015/0230802 A1 | 8/2015 | Lagodzki et al. | |
| 2015/0257763 A1 | 9/2015 | Blum et al. | |
| 2015/0265802 A1 | 9/2015 | Fukuoka et al. | |
| 2015/0272589 A1 | 10/2015 | Lorenzo | |
| 2015/0297240 A1 | 10/2015 | Divino et al. | |
| 2015/0327868 A1 | 11/2015 | Islak et al. | |
| 2015/0335333 A1 | 11/2015 | Jones et al. | |
| 2015/0342611 A1 | 12/2015 | Leopold et al. | |
| 2015/0343181 A1 | 12/2015 | Bradway et al. | |
| 2016/0008003 A1 | 1/2016 | Kleshinski et al. | |
| 2016/0022445 A1 | 1/2016 | Ruvalcaba et al. | |
| 2016/0030052 A1 | 2/2016 | Cragg et al. | |
| 2016/0166257 A1 | 6/2016 | Allen et al. | |
| 2016/0192942 A1 | 7/2016 | Strauss et al. | |
| 2016/0228123 A1 | 8/2016 | Anderson et al. | |
| 2016/0228124 A1 | 8/2016 | Trommeter et al. | |
| 2016/0228128 A1 | 8/2016 | Connolly | |
| 2016/0317274 A1 | 11/2016 | Liu et al. | |
| 2017/0014157 A1 | 1/2017 | Coyle et al. | |

FOREIGN PATENT DOCUMENTS

| | | |
|---|---|---|
| EP | 3085310 A1 | 10/2016 |
| JP | 2016537134 A | 12/2016 |
| WO | 0232496 A1 | 4/2002 |
| WO | 2007047111 A1 | 4/2007 |
| WO | 2007070797 A2 | 6/2007 |
| WO | 2010030993 A1 | 3/2010 |
| WO | 2010098804 A1 | 9/2010 |
| WO | 2014145012 A2 | 9/2014 |
| WO | 2014145005 A3 | 4/2015 |
| WO | 2017192394 A1 | 11/2017 |

OTHER PUBLICATIONS

PCT Application No. PCT/US2017/061779 International Search Report and Written Opinion, dated Feb. 26, 2018.

(56) References Cited

OTHER PUBLICATIONS

International Search Report and Written Opinion dated Jul. 13, 2018 for International Application No. PCT/US2018/028240.
International Search Report and Written Opinion dated Dec. 5, 2018 for International Application No. PCT/US2018/000148.
International Search Report and Written Opinion, PCT/US2018/044519, dated Oct. 30, 2018.

* cited by examiner

DILATOR WITH ENGAGEMENT REGION

CROSS-REFERENCE TO RELATED APPLICATIONS

This application claims the benefit of priority under 35 U.S.C. § 119 to U.S. Provisional Application Ser. No. 62/539,140, filed Jul. 31, 2017, the entirety of which is incorporated herein by reference.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer system is utilized to position an introducer sheath into the vessel, whereby the introducer sheath is utilized to facilitate the insertion of medical devices into the vessel. Vessel trauma resulting from forces applied to the vessel wall by a medical device may be lessened by minimizing the size of the introducer system used to access the vessel. Therefore, it may be desirable to design an introducer system having a reduced insertion profile.

SUMMARY

This disclosure provides design, material, manufacturing method, and use alternatives for medical devices. An example dilator includes a hub and an elongate shaft having a distal end region, a proximal end region and a cross-sectional profile. Additionally, the proximal end region of the elongate shaft is coupled to the hub and the elongate shaft is configured to extend through at least a portion of a lumen of an expandable introducer sheath. Additionally, the cross-sectional profile of the elongate shaft includes at least one engagement portion and at least a portion of the expandable introducer sheath extends into the at least one engagement portion of the dilator.

Alternatively or additionally to any of the examples above, wherein the engagement portion includes a projection extending radially away from the elongate shaft.

Alternatively or additionally to any of the examples above, wherein the elongate shaft includes a plurality of engagement portions.

Alternatively or additionally to any of the examples above, wherein the plurality of engagement portions are spaced around the circumference of the elongate shaft.

Alternatively or additionally to any of the examples above, wherein each of the plurality of engagement portions extends from the distal end region to the proximal end region.

Alternatively or additionally to any of the examples above, wherein the expandable introducer sheath includes a plurality of spine members embedded within a wall of the introducer sheath, and wherein each of the engagement portions of the dilator are radially offset from each of the plurality of spine members.

Alternatively or additionally to any of the examples above, further comprising a longitudinally extending spline member configured to extend into a recessed portion of the dilator.

Alternatively or additionally to any of the examples above wherein the spline member is removable.

Alternatively or additionally to any of the examples above, wherein at least a portion of the expandable introducer sheath is configured to be positioned between the spline member and the dilator.

Alternatively or additionally to any of the examples above, wherein removing the spline member permits the expandable introducer sheath to shift from a first unexpanded configuration to a second expanded configuration.

Another example dilator includes:
a hub; and
an elongate shaft having a distal end region, a proximal end region and a first engagement region extending along an outer surface of thereof;
wherein the proximal end region of the elongate shaft is coupled to the hub;
wherein the elongate shaft is configured to extend through at least a portion of a lumen of an expandable introducer sheath;
wherein the expandable introducer sheath includes a second engagement region;
wherein the first engagement region of the elongate shaft is keyed with the second engagement region of the expandable introducer sheath.

Alternatively or additionally to any of the examples above, wherein the first engagement region includes at least one projection extending radially away from the elongate shaft.

Alternatively or additionally to any of the examples above, wherein the first engagement region includes a plurality of projections extending radially away from an outer surface of the elongate shaft.

Alternatively or additionally to any of the examples above, wherein the plurality of projections are spaced around the circumference of the elongate shaft.

Alternatively or additionally to any of the examples above, wherein each of the plurality of projections extends from the distal end region to the proximal end region.

Alternatively or additionally to any of the examples above, wherein the expandable introducer sheath includes a plurality of spine members embedded within a wall of the introducer sheath, and wherein each of the plurality of projections of the elongate shaft are radially offset with each of the plurality of spine members.

Alternatively or additionally to any of the examples above, further comprising a longitudinally extending spline member configured to extend into the first engagement region of the elongate shaft.

Alternatively or additionally to any of the examples above, wherein the spline member is removable.

Alternatively or additionally to any of the examples above, wherein removing the spline member permits the expandable introducer sheath to shift from a first unexpanded configuration to a second expanded configuration.

An example method for treating a body lumen includes:
positioning an introducer system within the body lumen, the introducer system including:
an expandable introducer sheath; and a dilator extending through at least a portion of a lumen of an expandable introducer sheath, the dilator including:

a hub; and an elongate shaft having a distal end region, a proximal end region and a first engagement region extending along an outer surface of thereof;

wherein the proximal end region of the elongate shaft is coupled to the hub;

wherein the expandable introducer sheath includes a second engagement region;

wherein the first engagement region of the dilator is keyed with the second engagement region of the expandable introducer sheath;

removing the dilator from the lumen of the expandable introducer sheath; and shifting the introducer sheath from an unexpanded configuration to an expanded configuration.

The above summary of some examples is not intended to describe each disclosed embodiment or every implementation of the present disclosure. The Figures, and Detailed Description, which follow, more particularly exemplify these examples.

Figure 1:
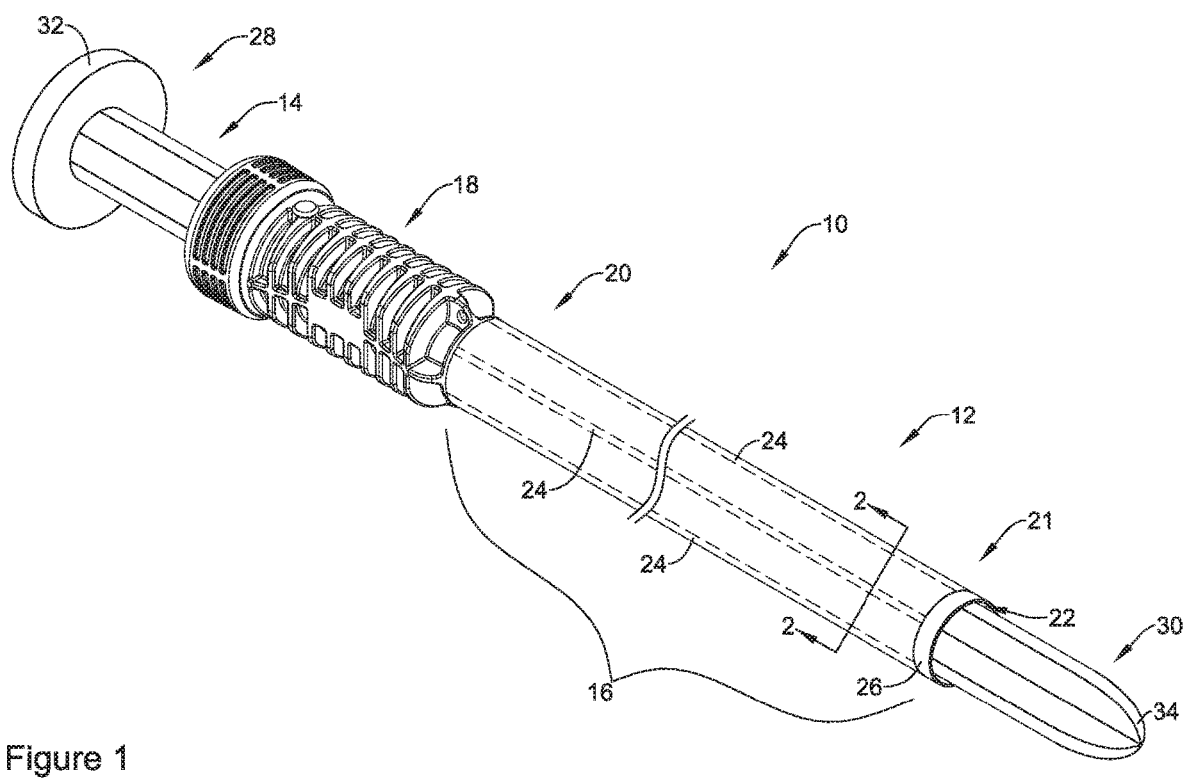
FIG. 1 is a perspective view of an example introducer system including an introducer and a dilator.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some examples", "other examples", etc., indicate that the embodiment described may include one or more particular features, structures, and/or characteristics. However, such recitations do not necessarily mean that all examples include the particular features, structures, and/or characteristics. Additionally, when particular features, structures, and/or characteristics are described in connection with one embodiment, it should be understood that such features, structures, and/or characteristics may also be used connection with other examples whether or not explicitly described unless clearly stated to the contrary.

The following detailed description should be read with reference to the drawings in which similar elements in different drawings are numbered the same. The drawings, which are not necessarily to scale, depict illustrative examples and are not intended to limit the scope of the disclosure.

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer sheath may be utilized to facilitate the insertion of medical devices into the vessel.

Further, in some instances, a dilator may be utilized in conjunction with an introducer sheath during insertion of the introducer sheath into the vessel. For example, in some instances, the dilator may be positioned within the lumen of the introducer sheath while a clinician inserts the introducer and dilator (in combination) into the body vessel. Additionally, in some instances it may be desirable to design the introducer system to have a reduced insertion profile. The following examples disclose an intravascular medical device including a dilator, whereby the dilator is designed to reduce the overall profile of an introducer sheath within which it is positioned.

FIG. 1 illustrates an example expandable introducer system 10. The introducer system 10 may include an expandable introducer sheath 12 and a dilator 14. As shown in FIG. 1 and described above, the dilator 14 may extend through a lumen 22 of the expandable introducer sheath 12.

The introducer sheath 12 may include a tubular member 16 attached to a hub member 18. The tubular member 16 may include a proximal section 20 and a distal section 21. The introducer sheath 12 may further include a lumen 22 extending therethrough. For example, both the tubular member 16 and the hub member 18 may each include the lumen 22 extending therethrough. In some examples, the tubular member 16 of the introducer 12 may have a substantially constant outer diameter. However, in other examples the introducer sheath 12 may include one or more tapered portions. It is contemplated that any portion of the introducer sheath 12 may include any number of tapers, constant diameter regions or combinations thereof.

The hub 18 may include a hemostatic valve or seal disposed therein. The hemostatic valve or seal may prevent blood or other bodily fluid(s) from flowing proximally through the lumen 22 of the tubular member 16. In at least some examples, the hub 18 may include a port in fluid communication with the lumen 22 of the tubular member 16.

As will be discussed in greater detail below, FIG. 1 illustrates that introducer sheath 12 may include one or more reinforcement members 24 extending along the tubular member 16. Further, in some examples it may be desirable to add a tip member to the distal end of any of the examples disclosed herein. FIG. 1 shows an example tip member 26 disposed along the tubular member 16. Tip member 26 may be designed with a low durometer material. In some instances, a lower durometer material may provide tip member 26 with the ability to radially expand (e.g., flex) outward and radially contract as a variety of medical devices are advanced through the tip member 26. Further, the tip member 26 may include a taper. For example, the tip member 26 may taper from a first diameter to a second diameter at the distal end of the introducer sheath 12. While not intended to be limiting, in some examples the shape of the tip member 26 may resemble a bull-nose. Additionally, the tip member 26 may include a radiopaque material. The radiopaque material may allow the tip member 26 to be visualized by a clinician during a medical procedure. In some examples, the tip member 26 may be segmented radially and/or dissected such that it may separate into segments upon expansion.

As shown in FIG. 1, the dilator 14 may extend through the lumen 22 of the introducer sheath 12. The dilator may include a proximal portion 28 and a distal portion 30. The proximal portion 28 may include a hub 32. The hub 32 may be utilized to grip and remove the dilator 14 from the introducer sheath 12. As will be discussed in greater detail below, the dilator 14 may include an outer surface profile which engages the profile of the lumen 22 of the introducer sheath 12.

The distal region 30 of the dilator 14 may include a tip 34. The tip 34 may include a taper. For example, the tip 34 may taper from a first diameter to a second diameter at the distal end of the dilator 14. The tip 34 may be designed to be atraumatic. While not intended to be limiting, in some examples the shape of the tip 34 may resemble a bull-nose. Additionally, the tip 34 may include a radiopaque material. The radiopaque material may allow the tip 34 to be visualized by a clinician during a medical procedure.

As discussed above, it can be appreciated that the dilator 14 may be sized such that the shape of the dilator 14 may support the structural integrity of the elongate member 16 of the introducer sheath 12 (e.g., provide radial and/or longitudinal support against collapse, buckling, etc.). For example, during insertion into a vessel, the dilator 14 may be positioned within the lumen 22 of introducer sheath 12. The dilator 14 and introducer sheath 12 (in combination) may be advanced through an access puncture site and into a body vessel.

Figure 2:
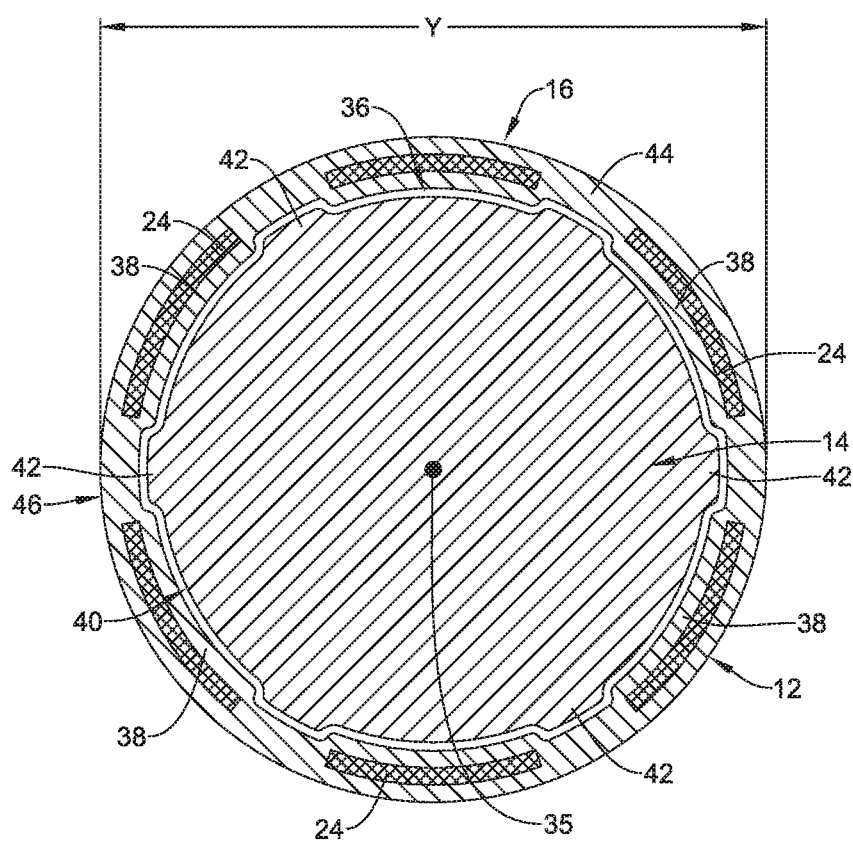
FIG. 2 is a cross-sectional view of the example introducer system of FIG. 1 taken along the line 2-2 of FIG. 1.

FIG. 2 shows a cross-sectional view along line 2-2 of FIG. 1. FIG. 2 illustrates a cross-section taken along the distal section 21 of the tubular member 16. As will be described in greater detail below, FIG. 2 represents a cross-section of the introducer system 10 described above with respect to FIG. 1. In other words, FIG. 2 illustrates the dilator 14 positioned (e.g., engaged) within the lumen 22 of the introducer sheath 12.

As shown in FIG. 2, the distal section 21 of the tubular member 16 may include an outer diameter depicted as "Y." Further, the tubular member 16 may include an inner surface 36. The inner surface 36 of the tubular member 16 may include one or more inwardly-extending projections 38. In other words, the inner surface 36 of the introducer sheath 12 may include one or more projections 38 which extend radially inward of the inner surface 36 of the introducer sheath 12.

FIG. 2 further illustrates the dilator 14 positioned with the lumen 22 of the introducer sheath 12. It can be appreciated from FIG. 2 that the dilator 14 has an outer surface profile 40 that engages with the profile of the inner surface 36 of the tubular member 16 of the introducer sheath 12. For example, FIG. 2 illustrates that the dilator 14 includes one or more outwardly-extending projections (e.g., ribs, etc.) 42. In other words, the outer surface 40 of the dilator 14 may include one or more projections 42 which extend radially outward from the outer surface 40 of the dilator 14. Further, while not illustrated in FIG. 1 or FIG. 2, it can be appreciated that projections 42 may extend along the entire length of the outer surface 40 of the dilator 14. In other words, the projections 42 may resemble ridges that extend from the distal portion 30 to the proximal portion 28 of the dilator 14.

Further, FIG. 2 illustrates that each of the projections 42 may be circumferentially spaced apart from one another around the longitudinal axis 35 of the of the dilator 14. In some instances, the projections 42 may be spaced substantially equidistant from one another. However, it is further contemplated that projections 42 may be spaced at variable distances around the longitudinal axis 35.

Additionally, it can further be appreciated from FIG. 2 that the outwardly-extending projections 42 of the dilator 14 may be positioned such they nest between two of the inwardly-extending projections 38 of the introducer sheath 12. In other words, the outer surface 40 profile of the dilator (including the outwardly-extending projections 42) may be "keyed" (e.g., engaged, mated, aligned, etc.) with the inner surface profile 36 of the introducer sheath (including the inwardly-extending projections 38). Further, FIG. 2 illustrates that each of the outwardly-extending projection 42 of the dilator 14 may be positioned between two inwardly-extending projections 38 of the introducer sheath 12. Further, FIG. 2 illustrates that each of the reinforcement members 24 may be radially aligned with the inwardly-extending projections 38 of the tubular member 16.

In some examples, the outwardly-extending projections 42 of the dilator 14 may be defined as a first engagement region of the dilator 14 and the inwardly-extending projections 38 of the introducer sheath may be defined as a second engagement region of the introducer sheath 12. As discussed above, the first engagement region of the dilator 14 may be keyed to (e.g., nested within, mated with) the second engagement region of the introducer sheath 12. It can be further appreciated that the ability of the first engagement region to nest within the second engagement region prevents the dilator 14 from rotating with respect to the introducer sheath 12. Additionally, it can be appreciated that "keying" the outer surface 40 of the dilator 14 with the inner surface 36 of the introducer sheath 12 permits the outer diameter of "Y" of the introducer sheath 12 to be minimized while still maintaining sufficient wall thickness portions of both the dilator 14 and the introducer sheath 12, whereby the introducer system 10 (as a whole) maintains sufficient structural integrity while being advanced into a body lumen.

FIG. 2 further illustrates the plurality of reinforcement members 24 positioned within the wall 44 of the tubular member 16. For example, FIG. 2 shows six reinforcement members 24 positioned circumferentially around the longitudinal axis 35 of the tubular member 16. However, while FIG. 2 shows six reinforcement members 24 positioned around the longitudinal axis 35 of the tubular member 16, it is contemplated that more greater or less than six reinforcement members 24 may be utilized for any example introducer systems 10 contemplated herein. For example, tubular member 16 may include 1, 2, 3, 4, 5, 6, 7, 8, 9, 10, 15 or more reinforcement members 24 positioned along tubular member 16. In some examples, the reinforcement members 24 may include one or more materials (e.g., nylon, Vestamid®, polyimide, polyester, metals, etc.) which are stiffer, higher durometer materials than the material for which the tubular member 16 is constructed.

Further, FIG. 2 shows that in some examples, the width of reinforcement members 24 may be substantially uniform. In other words, the width of reinforcement members 24 may remain substantially uniform along the length of the tubular member 16. However, it is contemplated that the width of one or more of the reinforcement members 24 may taper along the length of the tubular member 16.

Further, FIG. 2 shows that each of the reinforcement members 24 may be positioned radially outward of the inner surface 36 of the tubular member 16 and radially inward of the outer surface 46 of the tubular member 16. In other words, each of the reinforcement members 24 may be embedded (e.g., encased, surrounded, etc.) within the wall thickness "W" of the tubular member 16.

Additionally, FIG. 2 illustrates that each of the reinforcement members 24 may be circumferentially spaced apart from one another around the longitudinal axis 35 of the of the tubular member 16. In some instances, the reinforcement members 24 may be spaced substantially equidistant from one another. However, it is further contemplated that reinforcement members 24 may be spaced at variable distances around the longitudinal axis 35. For example, it is contemplated that in some examples the reinforcement members 24 may be asymmetrically arranged around the longitudinal axis 35. Further, FIG. 2 illustrates that each of the reinforcement members 24 may be radially aligned with the inwardly-extending projections 38 of the tubular member 16.

Figure 3:
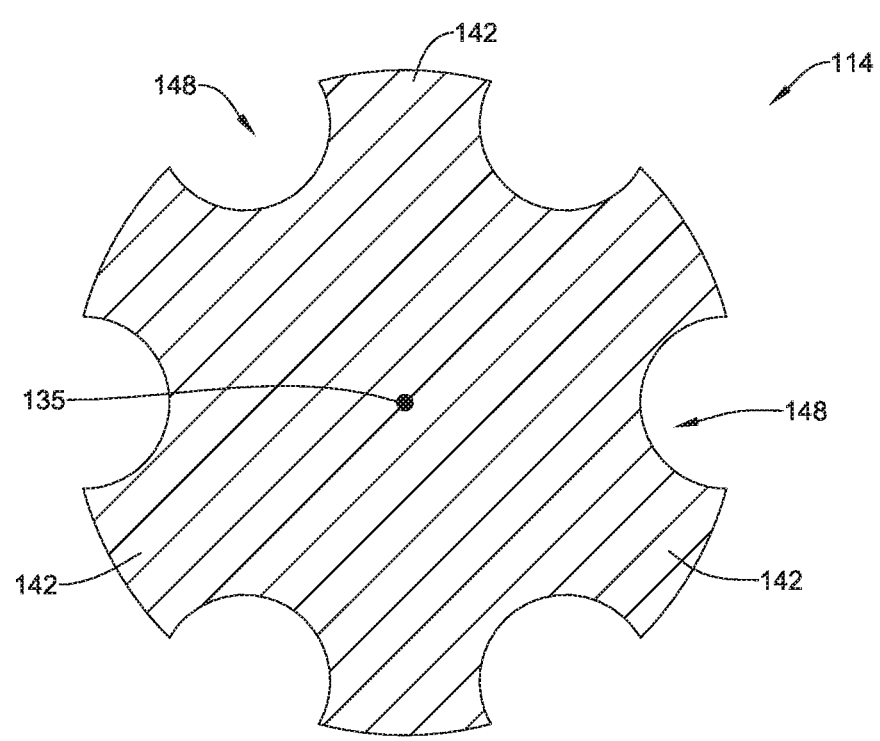
FIG. 3 is a cross-sectional view of an example dilator.

It can be appreciated that the example introducer systems 10 discussed herein may include a variety of different cross-sectional shapes and configurations. For example, FIG. 3 illustrates a cross-section an example dilator 114. Example dilator 114 may include a plurality of projections 142 spaced around the longitudinal axis 135 of the dilator 114. Additionally, the dilator 114 may include a plurality of recessed portions 148 positioned between adjacent projections 142 of the dilator 114. It can further be appreciated from the above discussion that an example introducer may be designed that include an inner surface profile that engages with the outer surface profile of the example dilator 114 shown in FIG. 3.

Figure 4:
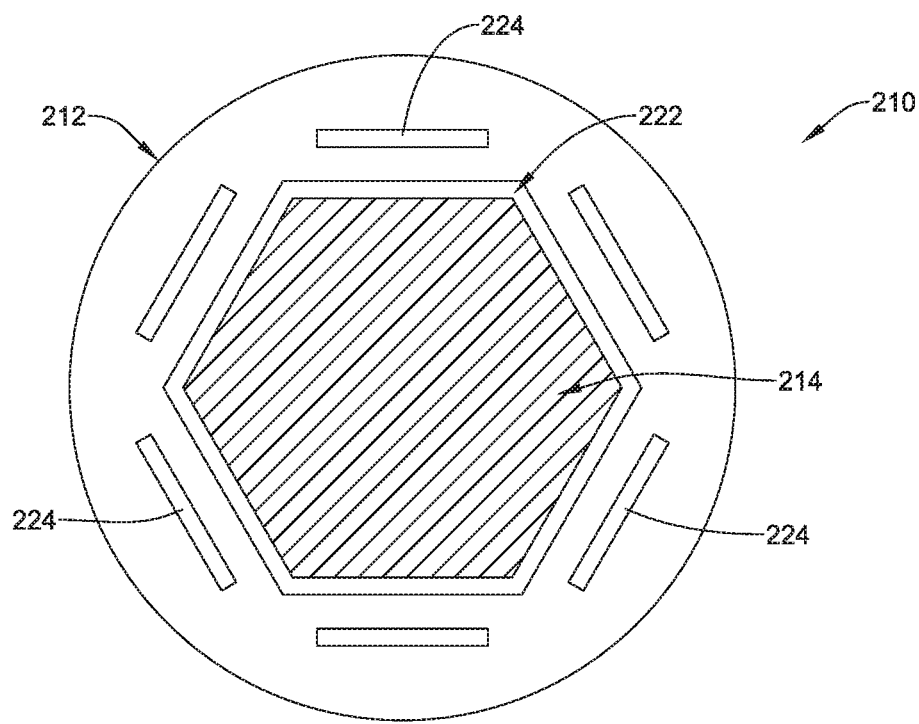
FIG. 4 is a cross-sectional view of another example dilator positioned within an example introducer.

FIG. 4 illustrates another example introducer system 210. Example introducer system 210 may be similar in form and function other introducer systems discussed herein. For example, introducer system 210 may include an example introducer sheath 212 and an example dilator 214. Dilator 214 may extend within a lumen 222 of the introducer sheath 212. Additionally, the introducer 212 may include a plurality of reinforcement members 224 positioned within the wall 244 of the introducer 212.

FIG. 4 illustrates that the cross-sectional profile of both the lumen 222 of the introducer sheath 212 and the outer surface profile of the dilator 214 is hexagonal. However, this is not intended to be limiting. Rather, it is contemplated that the cross-sectional shape of the both the lumen 222 of the introducer sheath 212 and the outer surface profile of the dilator 214 may be a variety of different geometries. For example, the cross-sectional shape of the dilator 214 may be square, oval, triangular, polygonal, rectangular, star-shaped, clover-shaped, etc. Additionally, FIG. 4 illustrates that each of the reinforcement members 224 may be radially aligned with a side (e.g., face) of the hexagonal-shaped dilator.

Figure 5:
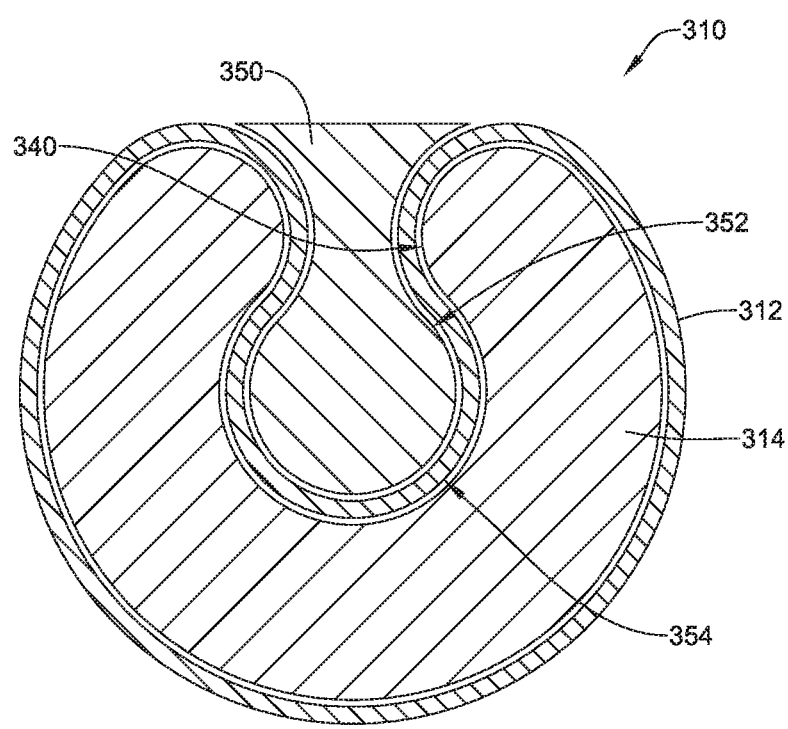
FIG. 5 is a perspective view of another example introducer system.

FIG. 5 illustrates another example introducer system 310. Introducer system 310 may be similar in form and function to other introducer systems disclosed herein. For example introducer system 310 may include an expandable introducer sheath 312 and a dilator 314. Further, dilator 314 may include channel 354 that extends radially inward from the outer surface 340 of the dilator. It can be appreciated that the channel 354 may extend from a distal region of the dilator 314 to the proximal portion of the dilator 314. In other words, channel 354 may alternatively be described as a recessed portion that extends longitudinally from the distal portion of the dilator 314 to the proximal portion of the dilator 314.

Additionally, FIG. 5 illustrates that a portion of the expandable introducer sheath 312 may be tucked (e.g., folded) into the channel 354. It can be appreciated that the portion of the introducer sheath 312 that is tucked into the channel 354 may extend along the entire length of the channel 354. It can be appreciated that tucking a portion of the introducer sheath 312 into the channel 354 may permit the outer diameter of the introducer sheath to be minimized. In other words, the outer diameter of the introducer sheath may be reduced by folding a portion of the introducer sheath into the channel 354 of the dilator 314.

FIG. 5 further illustrates that in some examples, the introducer system 310 may include a spline member 350. The spline member 350 may be designed to hold the folded portion of the expandable introducer 312 into the channel 354. For example, FIG. 5 illustrates that a portion of the spline member 350 may be inserted into the channel 354, whereby the wall of the expandable introducer sheath 312 is positioned between the spline member 350 and the dilator 314. Additionally, FIG. 5 illustrates that the spline member may include an enlarged portion 352 which nests within the channel 354. As shown in FIG. 5, it can be appreciated that the shape of the channel 354 may substantially match the shape of the enlarged portion 352. It can further be appreciated that designing the shaped of the enlarged portion 352 as shown in FIG. 5 will assist the spline member 350 from being removed from the channel 354 prematurely (and thereby allowing the introducer to expand prematurely). It can be appreciated that the enlarged portion 352 may be variety of different shapes and configurations while still being able to perform its function as described herein. For example, the spline member 350 may be triangular, rectangular, square, oval, etc.

Additionally, it can be appreciated that the spline member 350 may extend for the entire length or only a portion of the length of the channel 354. It can further be appreciated that the spline member 350 and/or the dilator 314 may be constructed from a materials that permit the spline member 350 to be removed from the channel 354. For example, it is contemplated that the spline member 350 and/or the dilator 314 may be constructed from materials that may flex and/or compress, thereby permitting the spline member 350 to be removed from the channel 354 while also being able to maintain the interference fit illustrated in FIG. 5.

Figure 6:
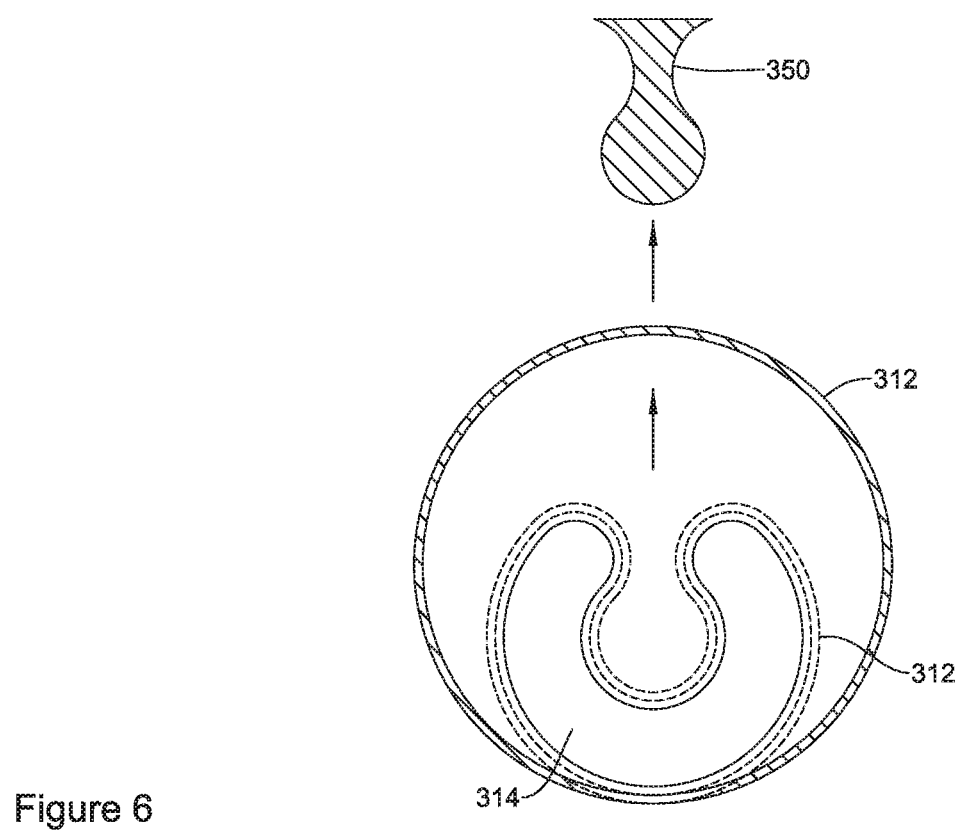
FIG. 6 is an illustration of the example introducer of FIG. 5 shifting from an unexpanded configuration to an expanded configuration.

FIG. 6 illustrates the shifting of the introducer sheath 312 (shown in FIG. 5) from an unexpanded configuration (depicted as a dashed line folded around the dilator 314) to an expanded configuration (depicted as a circle). The illustration shown in FIG. 6 depicts the expandable introducer sheath shifting from an unexpanded configuration to an expanded configuration after the spline member 350 has been removed from the dilator 314. The arrows in FIG. 6 represent a clinician removing the spline member 350 from the dilator 314. While not shown in FIG. 5 or FIG. 6, it is contemplated that a proximal region of the spline member 350 may include a hub member designed to permit a user to remove the spline member 350 from the dilator 350. As discussed above, after the spline member 350 has been removed from the dilator 314, the introducer sheath is permitted to shift from an unexpanded configuration to an expanded configuration.

Figure 7:
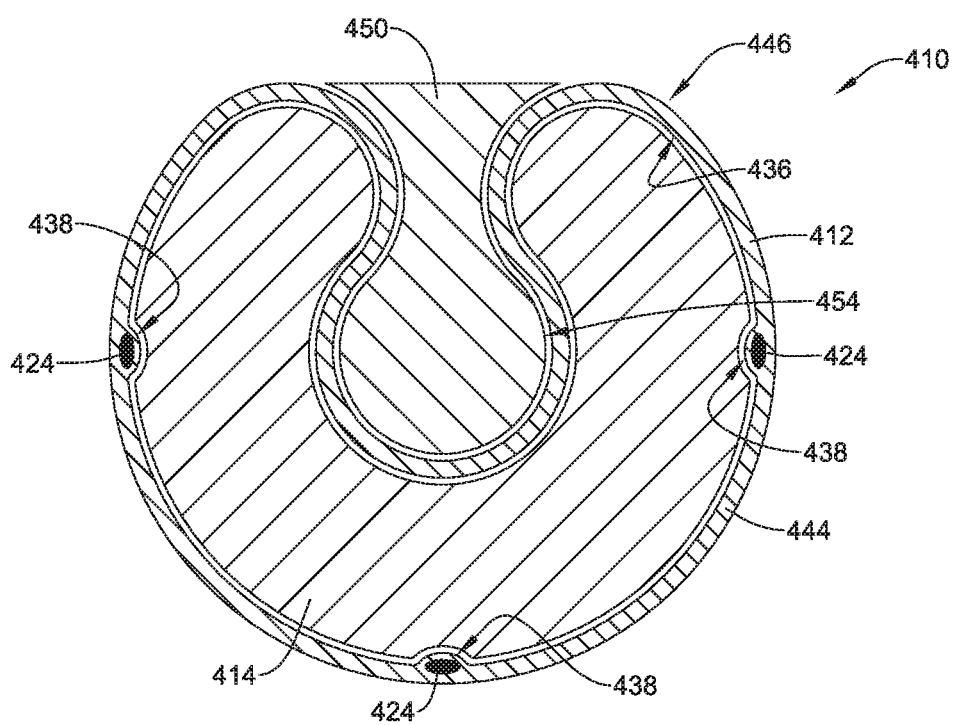
FIG. 7 is a cross-sectional view of another example introducer system.

FIG. 7 illustrates another example introducer system 410. Introducer system 410 may be similar in form and function to other introducer systems disclosed herein. For example introducer system 410 may include an expandable introducer sheath 412, a dilator 414 (including a channel 454) and a spline member 450 designed to engage with the dilator 414 via channel 454 as described above. Further, it can be appreciated that the channel 454 may extend from a distal region of the dilator 414 to a proximal region of the dilator 414.

Additionally, FIG. 7 further illustrates a plurality of reinforcement members 424 positioned within the wall 444 of the introducer sheath 412. For example, FIG. 7 shows three reinforcement members 424 positioned within the wall 444 of the introducer sheath 412. However, while FIG. 7 shows three reinforcement members 424 positioned within the wall 444 of the introducer sheath 412, it is contemplated that more or less than three reinforcement members 424 may be utilized. For example, the tubular member 416 may include 1, 2, 3, 4, 5, 6, 7, 8, 9, 10, 15 or more reinforcement members 424 within the wall 444 of the introducer sheath 412. In some examples, the reinforcement members 424 may include one or more materials (e.g., nylon, Vestamid®, polyimide, polyester, metals, etc.) which are stiffer, higher durometer materials than the material for which the introducer sheath 412 is constructed.

Further, FIG. 7 shows that in some examples, the cross-sectional shape of the reinforcement members 424 may be substantially uniform. Additionally, the width, thickness, etc. of the reinforcement members 424 may remain substantially uniform along the length of the introducer sheath 412. The reinforcement members 424 are substantially ovular-shaped in FIG. 7, however, this is not intended to be limiting. Rather, the cross-sectional shape of the reinforcement members 424 may triangular, rectangular, square, etc. However, it is contemplated that the cross-sectional shape of one or more the reinforcement members 424 may differ from other reinforcement members 424.

Further, FIG. 7 shows that each of the reinforcement members 424 may be positioned radially outward of the inner surface 436 of the introducer sheath 412 and radially inward of the outer surface 446 of the introducer sheath 412. In other words, each of the reinforcement members 424 may be embedded (e.g., encased, surrounded, etc.) within the wall thickness of the introducer sheath 412.

Additionally, FIG. 7 illustrates that each of the reinforcement members 424 may be spaced apart from one another. In some instances, the reinforcement members 424 may be spaced substantially equidistant from one another. However, it is further contemplated that reinforcement members 424 may be spaced at variable distances from one another. Further, FIG. 7 illustrates that each of the reinforcement members 424 may be radially aligned with the inwardly-extending projections 438 of the introducer sheath 412.

Figure 8:
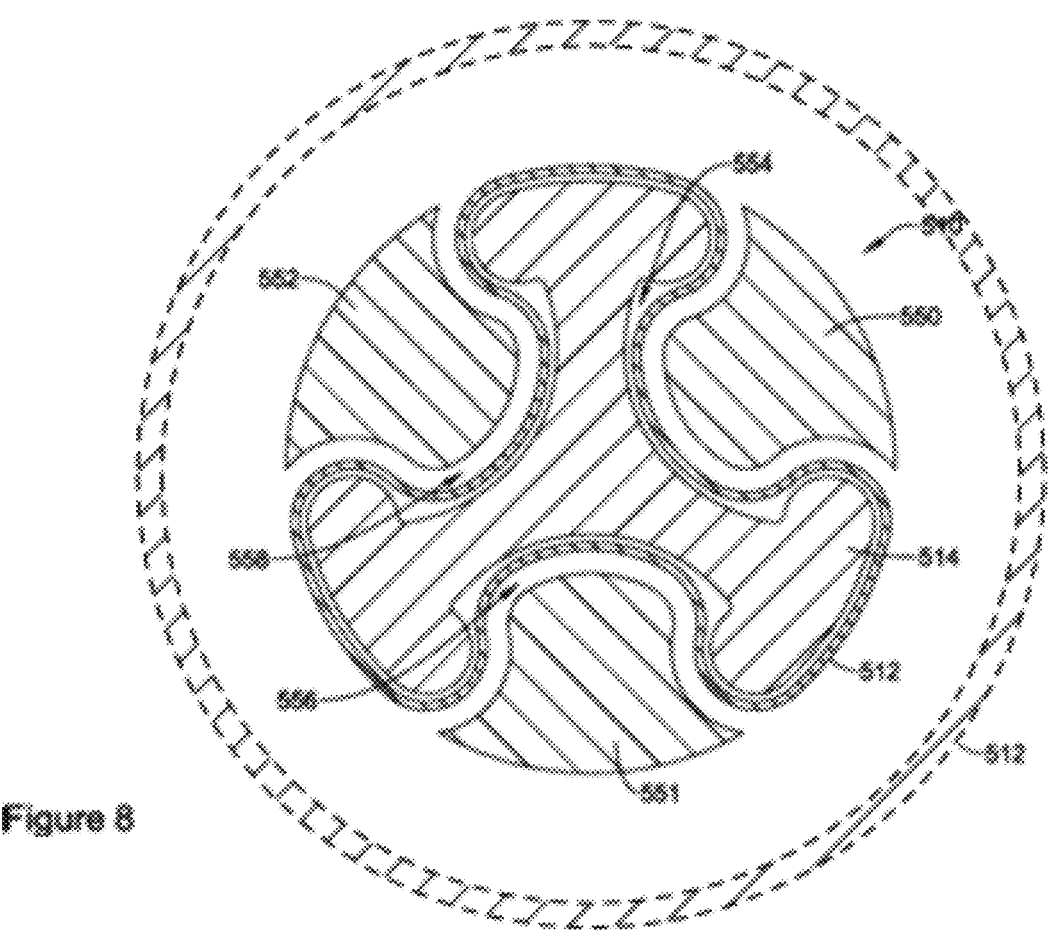
FIG. 8 is a cross-sectional view of another example introducer system.

FIG. 8 illustrates another example introducer system 510. Introducer system 510 may be similar in form and function to other introducer systems disclosed herein. For example, introducer system 510 may include an expandable introducer sheath 512 and a dilator 514. In an unexpanded configuration, expandable introducer sheath 512 is confined to follow the contours of dilator 524, while upon removal of the dilator 514 and/or spline members 550/551/552 of the dilator, the expandable introducer sheath is free to expand to an expanded configuration (depicted as a dashed circle 512). However, FIG. 8 illustrates that dilator 514 may include more than one channel. For example, FIG. 8 illustrates that dilator 514 may include a first channel 554, a second channel 556 and a third channel 558. Additionally, the introducer system 510 may include a first spline member 550 designed to engage with the dilator 514 via channel 554, a second spline member 551 designed to engage with the dilator 514 via channel 556 and a third spline member 552 designed to engage with the dilator 514 via channel 558. The introducer system 510 and components thereof (including channels 554/556/558 and spline members 550/551/552) may be constructed in a similar form and operate in a similar fashion to other channels and splines described herein. Further, while FIG. 8 depicts three separate splines and corresponding channels, this is not intended to be limiting. Rather, it is contemplated that the introducer system 510 (and other introducer systems described herein) may include more or less than three splines and corresponding channels.

Figure 9:
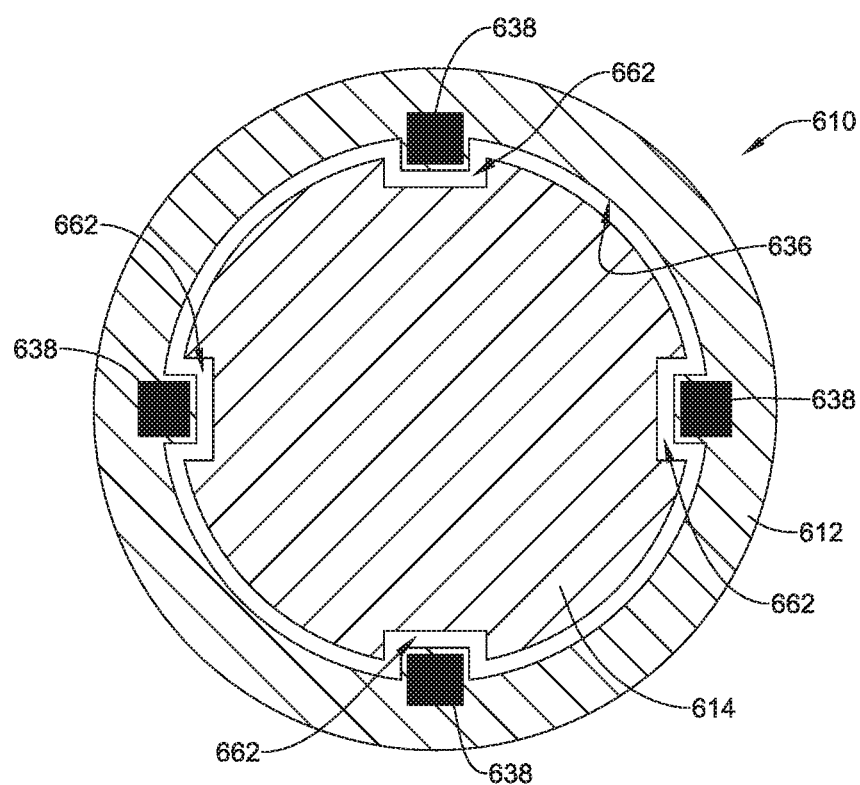
FIG. 9 is a cross-sectional view of another example introducer system including an introducer and a dilator.

FIG. 9 illustrates another example introducer system 610. Introducer system 610 may be similar in form and function to other introducer systems disclosed herein. For example introducer system 610 may include an expandable introducer sheath 612 and a dilator 614. Further, the introducer sheath 610 may include one or more reinforcement members 638 that extend radially inward from the inner surface 636 of the introducer sheath 612. Further, FIG. 9 shows that the dilator 614 may include one or more recessed portions 662 that radially align with the inwardly-extending reinforcement members 638. It is contemplated that both the reinforcement member 638 and the recessed portions 662 make extend along the entire length (e.g., from the distal portion to the proximal portion) of the introducer sheath 612 and the dilator, respectively. Further, both the expandable introducer sheath 612 and the dilator 614 may be constructed in a similar form and operate in a similar fashion to other introducer systems described herein.

Figure 10:
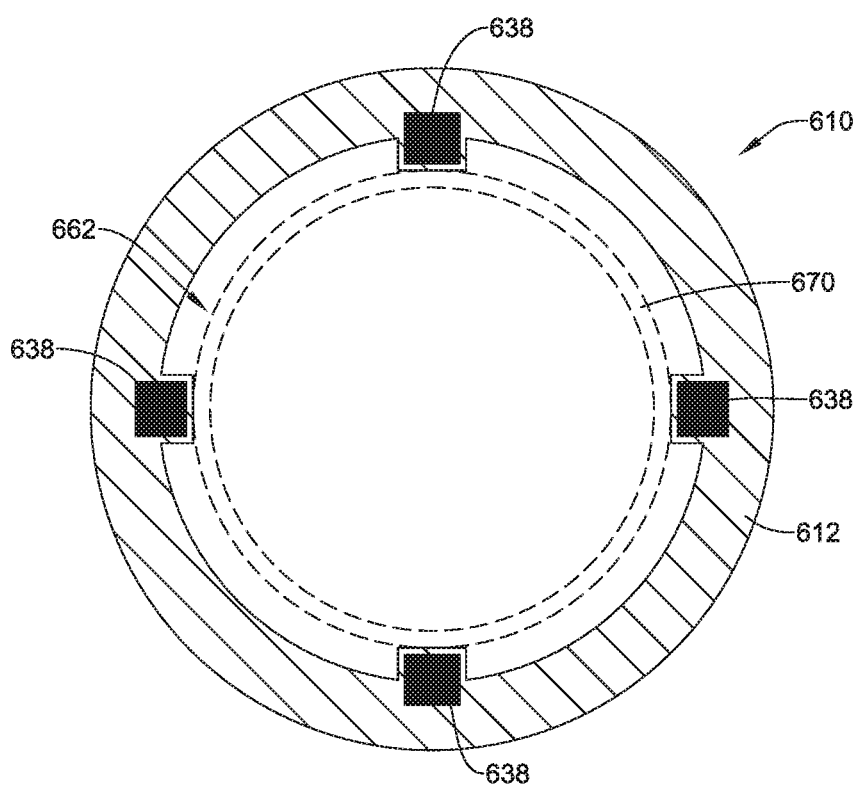
FIG. 10 is a cross-sectional view of the introducer shown in FIG. 9 after the dilator has been removed.

FIG. 10 illustrates that example introducer system 610 described with respect to FIG. 9. However, the dilator 614 has been removed from the introducer sheath 612 in FIG. 10. FIG. 10 illustrates that the inwardly-extending reinforcement members 638 may reduce the total surface area of the introducer sheath 612 which contacts an example medical device 670 positioned within the introducer sheath 612. For example, FIG. 10 illustrates that only surface area of the reinforcement members 638 may contact the example medical device 670 (verses the entire inner surface of the introducer sheath lumen 622). It can be appreciated that reducing surface area which contacts the example medical device 670 may reduce the amount of force required to advance the medical device through lumen 622 of the introducer sheath 612.

Further, it is contemplated that the inner surface and/or outer surface of any components of any of the introducer systems described herein may include one or more layers, liners or coatings, such as a lubricious coating, a hydrophilic coating, a hydrophobic coating, or other suitable coatings, liners, and the like, or may include a lubricant disposed thereon.

In some examples, introducer system 10 (or any other introducer system or components disclosed herein) may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some examples, the introducer system 10 (or any other introducer system or components disclosed herein) may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some examples, a suitable polymeric material may have a yield strain of at least 20%, at least 30%, at least 40%, at least 50%, or more. In some examples, the sheath, the membrane, and/or the plurality of corrugations may be made from a material having a low coefficient of friction. In some examples, the sheath, the membrane, and/or the plurality of corrugations may be formed from a fluoropolymer, such as polytetrafluoroethylene (PTFE) or fluorinated ethylene propylene (FEP).

Portions of introducer system 10 (or any other introducer system or components disclosed herein) may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other examples or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some examples, the devices may be deployed in a non-percutaneous procedure. Devices and methods in accordance with the disclosure can also be adapted and configured for other uses within the anatomy.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. A dilator, comprising:
a hub;
an elongate shaft having a distal end region, a proximal end region and a cross-sectional profile;
wherein the proximal end region of the elongate shaft is coupled to the hub;
wherein the elongate shaft is configured to extend through at least a portion of a lumen of an expandable introducer sheath;
wherein the cross-sectional profile of the elongate shaft includes at least one engagement portion, and wherein at least a portion of the expandable introducer sheath extends into the at least one engagement portion of the dilator; and
a longitudinally extending spline member configured to extend into a recessed portion of the dilator.

2. The dilator of claim 1, wherein the at least one engagement portion includes a projection extending radially away from the elongate shaft.

3. The dilator of claim 1, wherein the elongate shaft includes a plurality of engagement portions.

4. The dilator of claim 3, wherein the plurality of engagement portions is spaced around a circumference of the elongate shaft.

5. The dilator of claim 4, wherein each of the plurality of engagement portions extends from the distal end region to the proximal end region.

6. The dilator of claim 1, wherein the expandable introducer sheath includes a plurality of spine members embedded within a wall of the expandable introducer sheath, and wherein each of the engagement portions of the dilator are radially offset from each of the plurality of spine members.

7. The dilator of claim 1, wherein the spline member is removable.

8. The dilator of claim 7, wherein at least a portion of the expandable introducer sheath is configured to be positioned between the spline member and the dilator.

9. The dilator of claim 8, wherein removing the spline member permits the expandable introducer sheath to shift from a first unexpanded configuration to a second expanded configuration.

10. A dilator, comprising:
a hub;
a longitudinally extending spline member configured to extend into a recessed portion of the dilator; and an elongate shaft having a distal end region, a proximal end region, and a first engagement region extending along an outer surface of thereof;

wherein the proximal end region of the elongate shaft is coupled to the hub;

wherein the elongate shaft is configured to extend through at least a portion of a lumen of an expandable introducer sheath;

wherein the expandable introducer sheath includes a second engagement region;

wherein the first engagement region of the elongate shaft is keyed with the second engagement region of the expandable introducer sheath.

11. The dilator of claim 10, wherein the first engagement region includes at least one projection extending radially away from the elongate shaft.

12. The dilator of claim 10, wherein the first engagement region includes a plurality of projections extending radially away from an outer surface of the elongate shaft.

13. The dilator of claim 12, wherein the plurality of projections are spaced around a circumference of the elongate shaft.

14. The dilator of claim 13, wherein each of the plurality of projections extends from the distal end region to the proximal end region.

15. The dilator of claim 14, wherein the expandable introducer sheath includes a plurality of spine members embedded within a wall of the expandable introducer sheath, and wherein each of the plurality of projections of the elongate shaft are radially offset with each of the plurality of spine members.

16. The dilator of claim 10, further comprising a longitudinally extending spline member configured to extend into the first engagement region of the elongate shaft.

17. The dilator of claim 16, wherein the spline member is removable.

18. The dilator of claim 17, wherein removing the spline member permits the expandable introducer sheath to shift from a first unexpanded configuration to a second expanded configuration.

19. A method for treating a body lumen, the method comprising:

positioning an introducer system within the body lumen, the introducer system including:

an expandable introducer sheath;

a dilator extending through at least a portion of a lumen of an expandable introducer sheath, the dilator including:

a hub;

an elongate shaft having a distal end region, a proximal end region and a first engagement region extending along an outer surface of thereof;

wherein the proximal end region of the elongate shaft is coupled to the hub;

wherein the expandable introducer sheath includes a second engagement region;

wherein the first engagement region of the dilator is keyed with the second engagement region of the expandable introducer sheath; and a longitudinally extending spline member configured to extend into a recessed portion of the dilator removing the dilator from the lumen of the expandable introducer sheath; and shifting the expandable introducer sheath from an unexpanded configuration to an expanded configuration.

* * * * *